(12) United States Patent
Takii et al.

(10) Patent No.: US 12,343,082 B2
(45) Date of Patent: Jul. 1, 2025

(54) OPHTHALMOLOGIC MEASUREMENT APPARATUS, OPHTHALMOLOGIC MEASUREMENT SYSTEM, AND OPHTHALMOLOGIC MEASUREMENT PROGRAM

(71) Applicant: NIDEK CO., LTD., Aichi (JP)

(72) Inventors: Michihiro Takii, Aichi (JP); Masanori Yatani, Aichi (JP); Kazunari Shimizu, Aichi (JP); Tetsuya Yamamoto, Aichi (JP)

(73) Assignee: NIDEK CO., LTD., Aichi (JP)

(*) Notice: Subject to any disclaimer, the term of this patent is extended or adjusted under 35 U.S.C. 154(b) by 502 days.

(21) Appl. No.: 17/113,210

(22) Filed: Dec. 7, 2020

(65) Prior Publication Data

US 2021/0186322 A1 Jun. 24, 2021

(30) Foreign Application Priority Data

Dec. 13, 2019 (JP) .................. 2019-225722

(51) Int. Cl.
*A61B 3/103* (2006.01)
*A61B 3/00* (2006.01)
(Continued)

(52) U.S. Cl.
CPC ............ *A61B 3/103* (2013.01); *A61B 3/0025* (2013.01); *A61B 3/0033* (2013.01);
(Continued)

(58) Field of Classification Search
CPC .......... A61B 3/103; A61B 3/15; A61B 3/152; A61B 3/12; A61B 3/107; A61B 3/028; A61B 3/0025; A61B 3/0041; A61F 2/16
See application file for complete search history.

(56) References Cited

U.S. PATENT DOCUMENTS 6,409,345 B1 6/2002 Molebny et al.
7,556,378 B1 * 7/2009 Ianchulev .............. A61B 3/103
351/212

(Continued)

FOREIGN PATENT DOCUMENTS

EP 3 075 303 A1 10/2016
JP 2012-75647 A 4/2012

(Continued)

OTHER PUBLICATIONS

Huang, Tang, Wang, et al., Optical Coherence Tomography-Based Corneal Power Measurement and Intraocular Lens Power Calculation Following Laser Vision Correction, 2013, Trans Am Ophthalmol Soc 2013;111:34-45 (Year: 2013).*

(Continued)

*Primary Examiner* — Wyatt A Stoffa
*Assistant Examiner* — Samanvitha Sridhar
(74) *Attorney, Agent, or Firm* — Sughrue Mion, PLLC

(57) ABSTRACT

There is provided an ophthalmologic measurement apparatus for measuring a subject eye. The apparatus includes measurement means for objectively measuring eye refractive power of the subject eye, acquisition means for acquiring intraocular lens information relating to an intraocular (Continued)

lens inserted into the subject eye, and correction means for correcting a measurement result of the eye refractive power, based on the intraocular lens information.

18 Claims, 9 Drawing Sheets

(51) Int. Cl.
  *A61B 3/028* (2006.01)
  *A61B 3/107* (2006.01)
  *A61B 3/12* (2006.01)
(52) U.S. Cl.
  CPC ............ *A61B 3/0041* (2013.01); *A61B 3/028* (2013.01); *A61B 3/107* (2013.01); *A61B 3/12* (2013.01)

(56) References Cited

U.S. PATENT DOCUMENTS

| | | | |
|---|---|---|---|
| RE42,782 E | | 10/2011 | Molebny et al. |
| 10,136,809 B2 * | | 11/2018 | Hayashi ................. A61B 3/028 |
| 2003/0011745 A1 | | 1/2003 | Molebny et al. |
| 2004/0218142 A1 | | 11/2004 | Wakil et al. |
| 2005/0007551 A1 | | 1/2005 | Wakil et al. |
| 2005/0057723 A1 | | 3/2005 | Wakil et al. |
| 2006/0170868 A1 | | 8/2006 | Molebny et al. |
| 2013/0050643 A1 | | 2/2013 | Endo |
| 2014/0218685 A1 | | 8/2014 | Nakamura |
| 2015/0057989 A1 | | 2/2015 | Hacker et al. |
| 2015/0077705 A1 * | | 3/2015 | Artsyukhovich .... A61B 3/1015 351/206 |
| 2017/0273558 A1 * | | 9/2017 | Tamura .................... A61B 3/14 |

FOREIGN PATENT DOCUMENTS

| | | | | |
|---|---|---|---|---|
| JP | 2012075647 A | * | 4/2012 | |
| JP | 2014-147570 A | | 8/2014 | |
| WO | 2005/048819 A2 | | 6/2005 | |
| WO | WO-2019026862 A1 | * | 2/2019 | ............... A61B 3/10 |
| WO | WO-2020121661 A1 | * | 6/2020 | ............... A61F 2/16 |

OTHER PUBLICATIONS

Office Action issued Apr. 25, 2023, by the Japan Patent Office in counterpart Japanese Patent Application No. 2019-225722.
Extended European Search Report dated May 10, 2021, issued by the European Patent Office in counterpart European patent Application No. 20212408.7.
Ianchulev et al., "Intraoperative optical refractive biometry for intraocular lens power estimation without axial length and keratometry measurements," Journal Cataract and Refractive Surgery, vol. 31, Aug. 2005, pp. 1530-1536.

* cited by examiner

| No. | IOL | CORRECTION AMOUNT |
|---|---|---|
| 1 | △△△ | −0.5D |
| 2 | ××× | −1.0D |
| 3 | ○○○ | +0.4D |
| ⋮ | ⋮ | ⋮ |

FIG. 6

PATIENT A, PATIENT NUMBER : 1234

TYPE OF IOL : △△△

OPHTHALMOLOGIC MEASUREMENT APPARATUS, OPHTHALMOLOGIC MEASUREMENT SYSTEM, AND OPHTHALMOLOGIC MEASUREMENT PROGRAM

CROSS-REFERENCE TO RELATED APPLICATION

This application claims priority from Japanese Patent Applications No. 2019-225722 filed on Dec. 13, 2019, the entire subject-matter of which is incorporated herein by reference.

TECHNICAL FIELD

The present disclosure relates to an ophthalmologic measurement apparatus, an ophthalmologic measurement system, and an ophthalmologic measurement program for measuring eye refractive power of a subject eye.

BACKGROUND ART

For example, as an ophthalmologic measurement apparatus, an apparatus is known which objectively measures eye refractive power of a subject eye by projecting a measurement light flux onto a fundus of the subject eye and causing a light receiving element to receive a reflected light flux from the fundus (for example, refer to JP-A-2014-147570).

However, according to the apparatus in the related art, when the subject eye into which an intraocular lens is inserted is measured, an obtained objective measurement value may be different from a subjective measurement value which is subjectively measured.

SUMMARY

In view of the problem in the related art, the present disclosure aims to provide an ophthalmologic measurement apparatus, an ophthalmologic measurement system, and an ophthalmologic measurement program, which are capable of accurately measuring eye refractive power of a lens-inserted eye that is a subject eye into which an intraocular lens is inserted.

The present disclosure includes configurations as follows.

(1) There is provided an ophthalmologic measurement apparatus for measuring a subject eye, including: a measurement unit that objectively measures eye refractive power of the subject eye; an acquisition unit that acquires intraocular lens information relating to an intraocular lens inserted into the subject eye; and a correction unit that corrects a measurement result of the eye refractive power, based on the intraocular lens information.

(2) There is provided an ophthalmologic measurement system including: an ophthalmologic measurement apparatus that measures a subject eye; and a management server that stores intraocular lens information relating to an intraocular lens inserted into the subject eye, in which the management server includes a storage unit that stores the intraocular lens information in a state where the intraocular lens information is associated with identification information for identifying a subject, and in which the ophthalmologic measurement apparatus includes: a measurement unit that measures eye refractive power of the subject eye; an acquisition unit that acquires the identification information, and acquires the intraocular lens information associated with the identification information from the storage unit of the management server; and a correction unit that corrects a measurement result of the eye refractive power, based on the intraocular lens information.

(3) There is provided a non-temporary computer-readable medium storing an ophthalmologic measurement program, the ophthalmologic measurement program being executed by a processor in an ophthalmologic measurement apparatus for measuring a subject eye to cause the ophthalmologic measurement apparatus to execute a process including: a measurement step of measuring eye refractive power of the subject eye; an acquisition step of acquiring intraocular lens information relating to an intraocular lens inserted into the subject eye; and a correction step of correcting a measurement result of the eye refractive power, based on the intraocular lens information.

According to the present disclosure, eye refractive power can be accurately measured for a lens-inserted eye that is a subject eye into which an intraocular lens is inserted.

BRIEF DESCRIPTION OF DRAWINGS

FIG. 6 is an example of patient information stored in a management server.

DETAILED DESCRIPTION

Illustrative Embodiment

Figure 1:
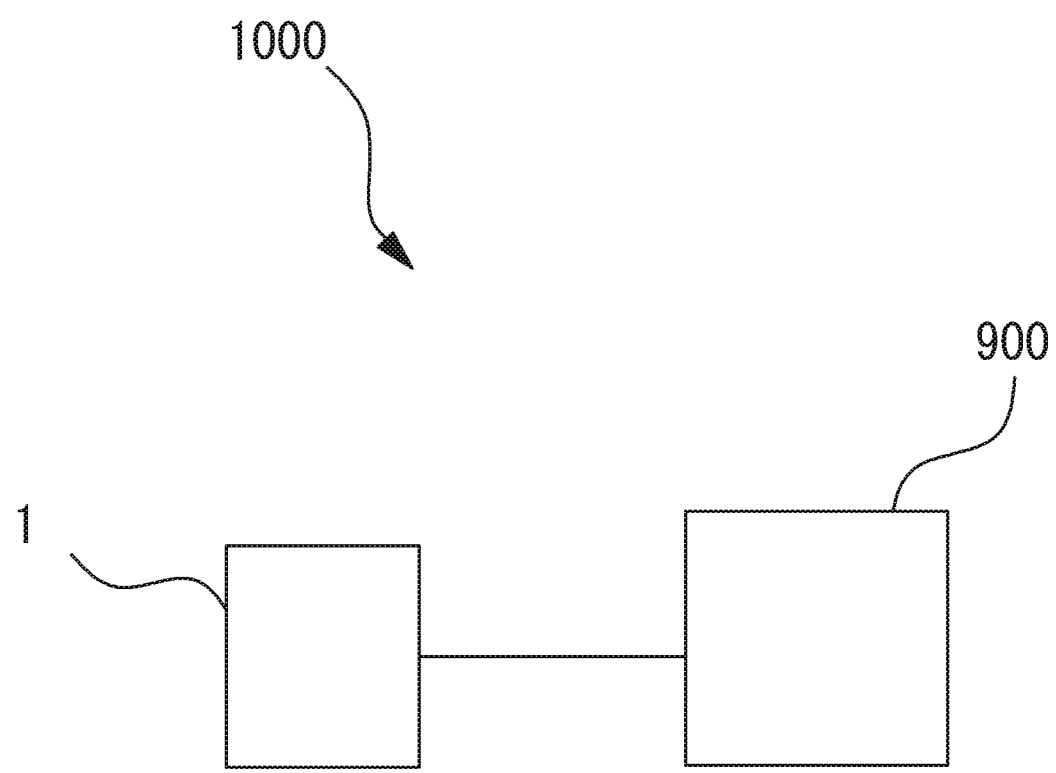
FIG. 1 is a schematic view of an ophthalmologic measurement system.

Hereinafter, illustrative embodiments according to the present disclosure will be described. An ophthalmologic measurement apparatus of the present illustrative embodiment (for example, an ophthalmologic measurement apparatus 1) is an apparatus that measures a subject eye. For example, an ophthalmologic measurement apparatus objectively measures eye refractive power (refraction degree) of the subject eye. The ophthalmologic measurement apparatus includes a measurement unit (for example, a measurement unit 100), an acquisition unit (for example, a control unit 70), and a correction unit (for example, the control unit 70).

For example, the measurement unit measures the eye refractive power of the subject eye. For example, the eye refractive power may be spherical information (for example, spherical power) or astigmatic information (for example, cylindrical power and astigmatic axis angle), or may be wave aberration information. For example, the measurement unit includes a measurement optical system (for example, a measurement optical system 200). The measurement optical system projects measurement light onto the subject eye, and receives the measurement light reflected by the subject eye to acquire a pattern image according to the eye refractive power. For example, a size or a shape of the pattern image varies in accordance with the eye refractive power of the subject eye. The pattern image may be a ring image. For example, the ring image is an image received by a light receiving element of the measurement optical system in a state where the measurement light is focused in a ring shape. In addition, the pattern image may be a plurality of point images (for example, a Hartmann image).

The acquisition unit acquires intraocular lens (IOL) information (hereinafter, referred to as IOL information) of the subject eye. For example, the IOL information is information relating to an IOL inserted into the subject eye. The IOL information may be information according to design conditions of the IOL, and for example, may be information relating to a type of IOL such as a brand, a model number, and a type (segmental type and a diffractive type) of the IOL. For example, the IOL information may include information such as power of the IOL or an orientation in which the IOL is inserted (rotation angle around an optical axis of the IOL).

The correction unit corrects a measurement result of the eye refractive power, based on the IOL information. For example, the correction unit may correct the spherical power, the cylindrical power, the astigmatic axis angle, and wave aberration, based on the IOL, information. In this manner, the ophthalmologic measurement apparatus of the present embodiment can acquire a more suitable measurement result even when a lens-inserted eye that is the subject eye into which the IOL is inserted is measured.

For example, the correction unit may correct the measurement result of the eye refractive power, based on a correction amount set in accordance with the type of the IOL. A deviation amount of the eye refractive power varies in accordance with the type of the IOL. Accordingly, the measurement result of the eye refractive power may be corrected in accordance with the correction amount set for each type of the IOL. In this manner, suitable eye refractive power of the subject eye can be easily acquired. In addition, for example, the correction unit may correct the measurement result of the eye refractive power, based on the correction amount set in accordance with design conditions of the IOL. In this manner, the more suitable measurement result can be acquired even when the measurement value deviates due to the design conditions of the IOL.

In the IOL inserted into the subject eye, the correction unit may correct the measurement result of the eye refractive power, based on the correction amount set in accordance with the orientation of the IOL. In this manner, the cylindrical power or the astigmatic axis angle can be easily corrected.

The acquisition unit may acquire IOL information from a management server (for example, a management server 900). For example, the management server stores the IOL information of the subject eye. In this manner, even when the IOL information of a subject is not stored in the ophthalmologic measurement apparatus, the eye refractive power can be corrected, based on the IOL information acquired from the management server.

The acquisition unit may acquire identification information (for example, ID and identification number) for identifying the subject. In this case, the acquisition unit may acquire the IOL information associated with the subject by the identification information. For example, the management server stores the subject and the IOL information in a state where both are associated with each other by the identification information. Therefore, the ophthalmologic measurement apparatus may receive the IOL information associated with the identification information from the management server by transmitting the identification information of the subject to the management server.

The apparatus may include an input receiving unit (for example, a control unit 70). The input receiving unit receives an operation input from an examiner. For example, the input receiving unit receives an operation signal output from an operation unit (for example, an operation unit 76) by an operation of the examiner. In this case, the acquisition unit may acquire the IOL information, based on the operation input received by the input receiving unit. In this manner, the ophthalmologic measurement apparatus can correct the measurement result of the eye refractive power even in a state where the ophthalmologic measurement apparatus is not connected to the management server or the like.

The apparatus may include a display control unit (for example, the control unit 70). The display control unit causes a display unit (for example, a display unit 75) to display an IOL selection screen. For example, the IOL selection screen is a screen for selecting a type of the intraocular lens inserted into the subject eye. The IOL selection screen enables the examiner to easily designate the type of intraocular lens inserted into the subject eye.

The apparatus may include an output unit. For example, the output unit may be a display unit or a printer. For example, the output unit outputs both the measurement result obtained before correction and the measurement result obtained after correction. For example, the output unit may cause a display screen to simultaneously display the measurement results before and after the correction, or may simultaneously print the measurement results on printing paper. In this manner, the examiner can easily confirm a correction degree of the measurement result.

The apparatus may include a notification unit. For example, the notification unit may be a display unit, a printer, a speaker, or a light. For example, the notification unit may notify that the measurement result has been corrected. In this manner, the examiner can easily recognize whether or not the measurement result has been corrected.

EXAMPLES

Hereinafter, examples according to the present disclosure will be described. As illustrated in FIG. 1, an ophthalmologic measurement system 1000 of the present example is configured to include an ophthalmologic measurement apparatus 1 and a management server 900. The ophthalmologic measurement apparatus 1 is an apparatus for measuring the subject eye. The management server 900 stores and manages patient information relating to a cataract surgery or the like.

<Ophthalmologic Measurement Apparatus>

Figure 2:
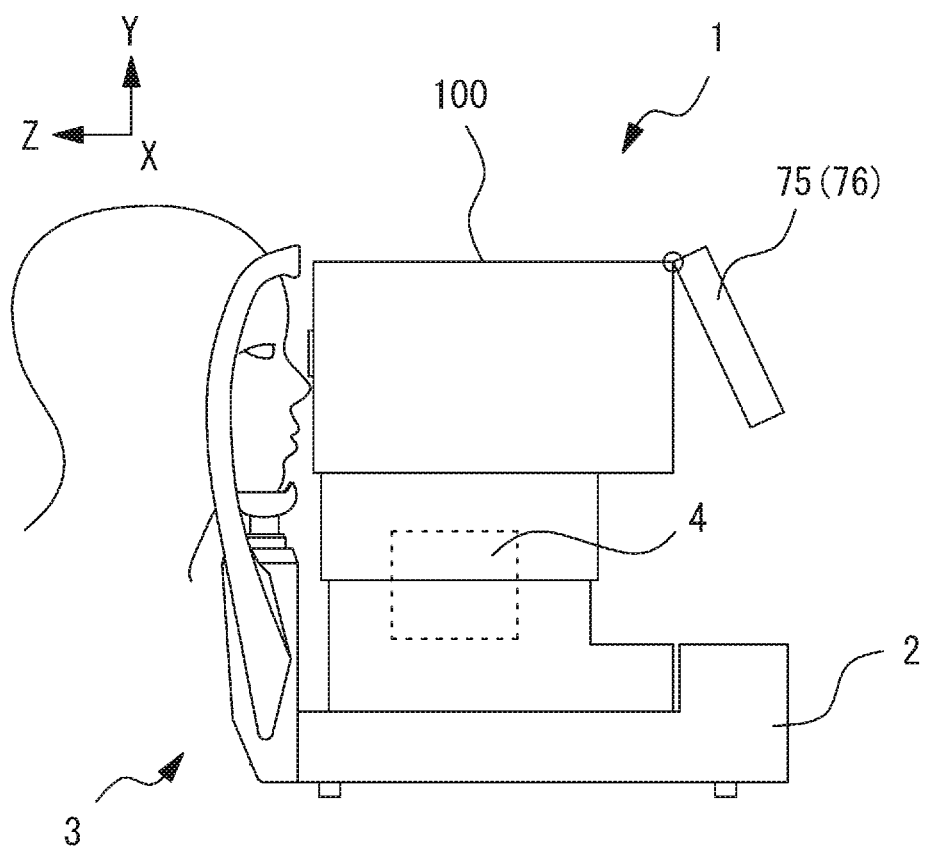
FIG. 2 is an external configuration diagram of an ophthalmologic measurement apparatus.

FIG. 2 is an external configuration diagram of the ophthalmologic measurement apparatus 1. For example, the ophthalmologic measurement apparatus 1 includes a base 2, a face support unit 3, a drive unit 4, a display unit 75, an operation unit 76, and a measurement unit 100 or the like. The face support unit 3 is fixed to the base 2 to support a face of a subject. The drive unit 4 drives the measurement unit 100 with respect to the base 2 in XYZ-directions. The display unit 75 displays various information (for example, an observation image of the subject eye and a measurement result of the subject eye or the like). The operation unit 76 performs various settings. In the present example, the display unit 75 provided with a touch panel also functions as the operation unit 76. The measurement unit 100 accommodates an optical system (to be described later). In the present example, as illustrated in FIG. 2, a rightward-leftward direction of the ophthalmologic measurement apparatus 1 will be referred to as an X-direction, an upward-downward direction will be referred to as a Y-direction, and a forward-rearward direction will be referred to as a Z-direction.

Figure 3:
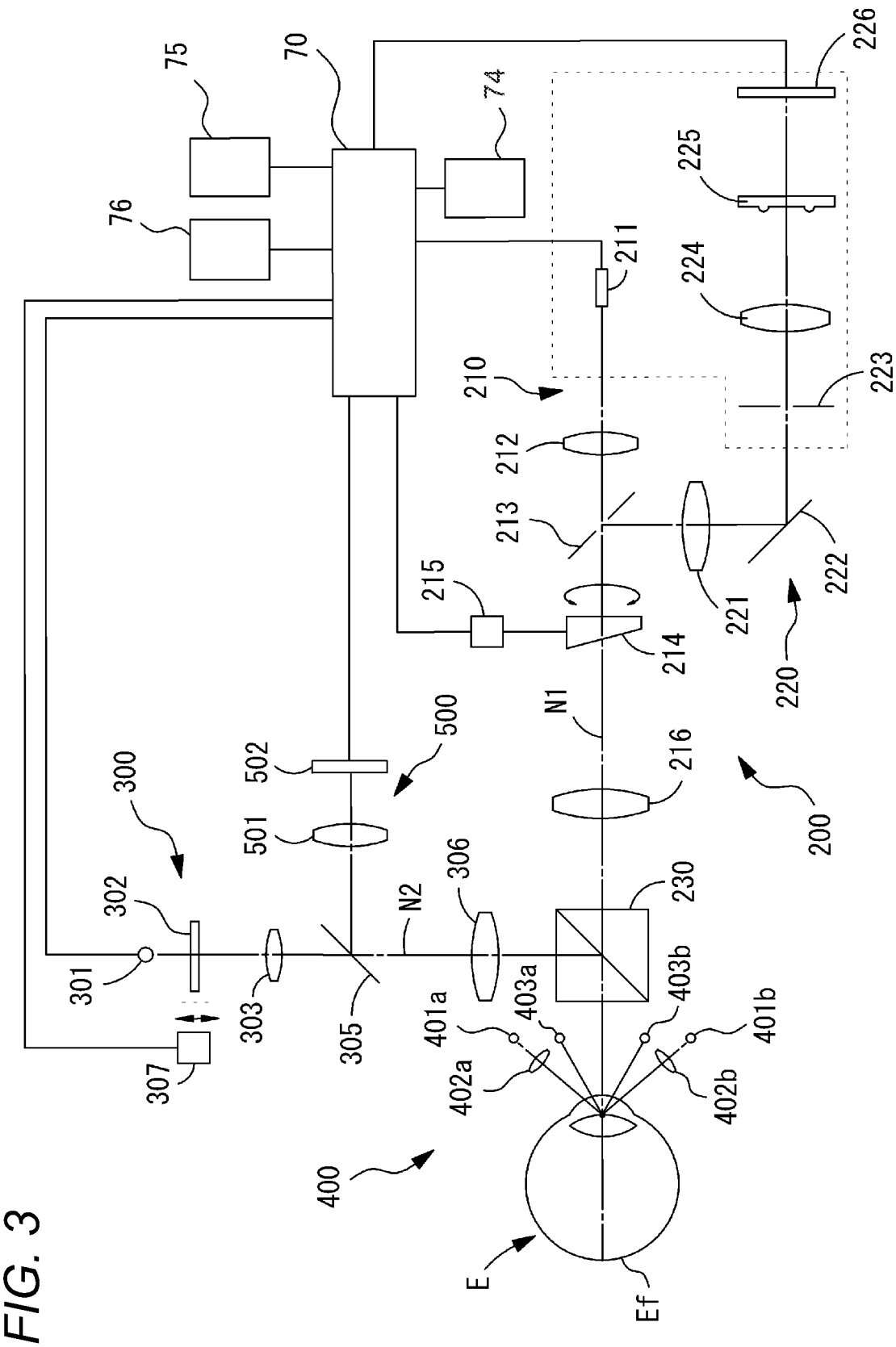
FIG. 3 is a schematic configuration diagram of an optical system and a control system.

FIG. 3 is a schematic configuration diagram of an optical system and a control system of the ophthalmologic measurement apparatus 1. For example, the measurement unit 100 includes a measurement optical system 200, a fixation target optical system 300, an index projection optical system 400, and an observation optical system 500. The measurement optical system 200 objectively measures the eye refractive power of a subject eye E (for example, spherical power, cylindrical power, or astigmatic axis angle). The fixation target optical system 300 presents a fixation target to the subject eye E. The index projection optical system 400 projects an alignment index for detecting the Z-direction of the subject eye E. The observation optical system 500 images an anterior segment of the subject eye E.

<Measurement Optical System>

For example, the measurement optical system 200 includes a light projecting optical system 210 and a light receiving optical system 220. The light projecting optical system 210 projects a spot-shaped measurement light flux onto a fundus Ef of the subject eye E via a central portion of a pupil in the subject eye E. The light receiving optical system 220 extracts a reflected light flux of the measurement light flux reflected by the fundus Ef in a ring shape via a peripheral portion of the pupil.

For example, the light projecting optical system 210 includes a light source 211, a relay lens 212, a hole mirror 213, a prism 214, a drive unit 215, and an objective lens 216. The light source 211 is disposed on an optical axis N1 of the measurement optical system 200, and has a positional relationship optically conjugate with the fundus Ef. For example, as the light source 211, a light emitting diode (LED) or a superluminescent diode (SLD) can be used. An opening portion of the hole mirror 213 has a positional relationship optically conjugate with the pupil. The prism 214 is disposed at a position away from a position conjugate with the pupil, and causes the light flux passing through the prism 214 to be eccentric with respect to the optical axis N1. Instead of the prism 214, a parallel flat plate may be diagonally disposed on the optical axis N1. The drive unit 215 drives the prism 214 to rotate around the optical axis N1.

The measurement light source 211 is used to project a spot-shaped measurement index onto the fundus Ef via the pupil. It is desirable that the light source 211 emits light in an infrared region in which a subject is less likely to feel glare. However, a configuration is not necessarily limited thereto. In addition, in the present example, the light source 211 is also used as an illumination light source for capturing a transillumination image of the subject eye E. That is, an inner portion of the pupil of the subject eye E is illuminated by fundus reflected light of a light flux (illumination light) emitted from the light source 211.

For example, the light receiving optical system 220 includes an objective lens 216, a prism 214, a hole mirror 213, a relay lens 221, a total reflection mirror 222, a light receiving diaphragm 223, a collimator lens 224, a ring lens 225, and an image sensor 226. The objective lens 216, the prism 214, and the hole mirror 213 are shared with the light projecting optical system 210. The relay lens 221 and the total reflection mirror 222 are disposed in a reflection direction of the hole mirror 213. The light receiving diaphragm 223, the collimator lens 224, the ring lens 225, and the image sensor 226 are disposed in a reflection direction of the total reflection mirror 222. The light receiving diaphragm 223 has a positional relationship optically conjugate with the fundus Ef. The ring lens 225 has a positional relationship optically conjugate with the pupil. For example, the ring lens 225 is configured to include a lens portion in which a cylindrical lens is formed in a ring shape, and a light-blocking portion to which light-blocking coating is applied except for the lens portion. The image sensor 226 has a positional relationship optically conjugate with the fundus Ef. For example, as the image sensor 226, a charge-coupled device (CCD) or a complementary metal-oxide-semiconductor (CMOS) can be used. For example, an output signal from the image sensor 226 is input to the control unit 70.

A beam splitter 230 is disposed between the subject eye E and the objective lens 216. The beam splitter 230 guides the measurement light flux from the fixation target optical system 300 to the subject eye E, and guides the reflected light flux from the anterior segment of the subject eye E to the observation optical system 500.

In the above-described configuration, the measurement light flux emitted from the light source 211 projects a spot-shaped measurement light flux onto the fundus Ef via the relay lens 212, the hole mirror 213, the prism 214, the objective lens 216, and the beam splitter 230. In this manner, a point light source image is formed on the fundus Ef. At this time, the prism 214 is rotated around the optical axis N1, and a pupil projection image (projected light flux on the pupil) of an opening portion of the hole mirror 213 is eccentrically rotated at high speed. The reflected light flux of the measurement light flux reflected by the fundus Ef is reflected by the hole mirror 213 via the beam splitter 230, the objective lens 216, and the prism 214. The reflected light flux is further reflected by the total reflection mirror 222 via the relay lens 221, and is focused on a position of the light receiving diaphragm 223. A ring-shaped image is formed on the image sensor 226 by the collimator lens 224 and the ring lens 225.

The measurement optical system 200 is not limited to the above-described configuration, and may be any desired measurement optical system having the light projecting optical system that projects the measurement light flux onto the fundus Ef of the subject eye E and the light receiving optical system that receives the reflected light flux of the measurement light flux reflected by the fundus Ef. For example, the measurement optical system 200 may be the measurement optical system that detects the reflected light flux of a spot index in the fundus Ef by projecting the spot index onto the fundus Ef and using a Shack-Hartmann sensor.

<Fixation Target Optical System>

For example, the fixation target optical system 300 includes a light source 301, a fixation target plate 302, a projection lens 303, a half mirror 305, an objective lens 306, and a drive unit 307. The light source 301 is disposed on an optical axis N2 coaxial with the optical axis N1 by the beam splitter 230. The fixation target plate 302 is used when objective eye refractive power of the subject eye E is measured. The drive unit 307 moves a position of the fixation target plate 302 is moved in a direction of the optical axis N2. In this manner, the drive unit 307 can move a presentation position of the fixation target to be presented to the subject eye E. In addition, the drive unit 307 can apply cloudy fog to the subject eye E by moving the light source 301 and the fixation target plate 302 in the direction of the optical axis N2. For example, as the drive unit 307, an actuator (for example, a stepping motor) and a photo interrupter serving as a reference position may be used in combination with each other.

<Index Projection Optical System>

The index projection optical system 400 includes a first index projection optical system and a second index projection optical system. The first index projection optical system projects an infinitely distant alignment index onto a cornea of the subject eye E. The second index projection optical system projects a finitely distant alignment index onto the cornea of the subject eye E.

For example, the first index projection optical system has point light sources 401a and 401b and collimator lenses 402a and 402b. For convenience, FIG. 3 illustrates only a portion of the first index projection optical system. The point light sources 401a and 401b may be light sources that emit near-infrared light. The collimator lenses 402a and 402b convert the light flux emitted from the point light source into a parallel light flux (substantially parallel light flux). A plurality of the point light sources and collimator lenses are disposed at an interval of 45 degrees on a concentric circle formed around the optical axis N1, and are bilaterally symmetrical across a vertical plane passing through the optical axis N1. In this manner, the infinitely distant alignment index is projected onto the cornea of the subject eye E.

For example, the second index projection optical system has point light sources 403a and 403b. For convenience, FIG. 3 illustrates only a portion of the second index projection optical system. The point light sources 403a and 403b may be light sources that emit near-infrared light. For example, the point light sources are disposed at positions different from those of the point light sources of the first index projection optical system. In this manner, the finitely distant alignment index is projected onto the subject eye E.

In the present example, a configuration in which the point-shaped light source is used as the light source of the first index projection optical system and the second index projection optical system has been described as an example. However, the present disclosure is not limited thereto. For example, a ring-shaped light source or a line-shaped light source may be used as the light source. In addition, the second index projection optical system can also be used as anterior segment illumination for illuminating the anterior segment of the subject eye E, or an index for measuring a corneal shape of the subject eye E.

<Observation Optical System>

For example, the observation optical system 500 includes the objective lens 306, the half mirror 305, an imaging lens 501, and an image sensor 502. The objective lens 306 and the half mirror 305 are shared with the fixation target optical system 300. The imaging lens 501 and the image sensor 502 are disposed in the reflection direction of the half mirror 305. The image sensor 502 has a positional relationship optically conjugate with the anterior segment of the subject eye E. The image sensor 502 captures a frontal image of the anterior segment of the subject eye E. The transillumination image which is a type of the anterior segment image is also captured by the image sensor 502. For example, an output from the image sensor 502 is input to the control unit 70 and the display unit 75. The observation optical system 500 also functions as the optical system that detects an alignment index image formed on the cornea of the subject eye E by the index projection optical system 400, and the control unit 70 detects a position of the alignment index image.

<Control Unit>

For example, the control unit 70 includes a CPU (processor), a RAM, and a ROM. The CPU controls driving of each unit in the ophthalmologic measurement apparatus 1. The RAM temporarily stores various types of information. Various programs executed by the CPU are stored in the ROM. The control unit 70 may be configured to include a plurality of control units (that is, a plurality of processors).

The drive unit 4, the display unit 75 (operation unit 76), and a non-volatile memory 74 (hereinafter, referred to as a memory 74) are electrically connected to the control unit 70. In addition, each light source, each image sensor, and each drive unit which are included in the measurement unit 100 are electrically connected to the control unit 70.

The memory 74 is a non-transient storage medium that can hold storage contents even when power supply is cut off. For example, as the memory 74, a hard disk drive, a flash ROM, or a detachable USB memory can be used.

Figures 4, 5:
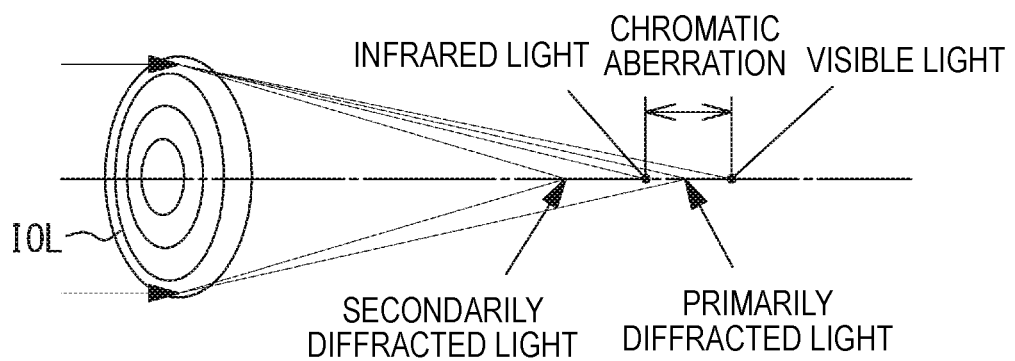
FIG. 4 is a view illustrating a correction table.
FIG. 5 is a view for describing a deviation of a measurement value.

In the memory 74 of the present example, correction data for correcting the measurement value is stored in advance. In a case of measuring the subject eye into which a multi-focal IOL is inserted, the control unit 70 corrects the measurement value by using the correction data stored in the memory 74. In this manner, objective refractive power (objective value) can be corrected to a value approximately the same as a value of subjective refractive power (subjective value) in the lens-inserted eye that is the subject eye into which the multifocal IOL is inserted. For example, the correction data is a correction amount set for each type of the IOL. For example, the correction data may be set for each brand of the IOL, or may be set for each model number of the IOL. As illustrated in FIG. 4, in the memory 74, the type of IOL and the correction amount of the measurement value corresponding thereto are stored as a correction table.

<Regarding Deviation of Measurement Value>

Chromatic aberration is one reason of a deviation between the subjective value and the objective value. The subjective value is dominated by influence of visible light (wavelength near green). However, when the measurement light used for objective measurement is not the visible light, or when the measurement light includes the visible light having a wavelength far from green (for example, red), a bending degree of the measurement light passing through the subject eye and the IOL is different from that of subjective measurement. Consequently, the deviation occurs between the subjective value and the objective value.

For example, in a case of the IOL having a diffraction structure to obtain long-sight power (refractive power for long-sight), especially in a case of the IOL designed to output the long-sight power with light other than a zero-order, the bending degree of the light differs between the visible light and the infrared light. As illustrated in FIG. 5, in the IOL having a certain diffraction structure, primary diffraction is dominant in diffraction efficiency of the infrared light. In this case, the ophthalmologic measurement apparatus 1 calculates the objective value by using primarily diffracted light. In a case of the primarily diffracted light, the infrared light is more greatly bent than the visible light. That is, the chromatic aberration on the axis is generated. Normally, in the measurement of the eye refractive power, the value obtained in view of the chromatic aberration of the diffraction is not calculated. Due to the influence of the chromatic aberration, in a case of FIG. 5, as the objective value calculated by the infrared light, a value closer to myopia is calculated with respect to the measurement value calculated by the visible light. The power deviation is determined by a design of the IOL and a wavelength band of the measurement light. Therefore, when a certain IOL is measured by a certain ophthalmologic measurement apparatus, a deviation amount of the refractive power has a fixed value.

The deviation amount of the refractive power differs depending on the design of the diffraction of the IOL. For example, depending on design conditions such as which order of the diffraction is used in the design of the long-sight power or which material is to be used, a degree of the correction to either a myopia side or a hyperopia side is changed. In the present example, the deviation amount between the visible light and the infrared light is obtained in advance for each type of the IOL by an experiment or a simulation, and the correction amount to be stored in the memory 74 is determined, based on the deviation amount.

<Management Server>

Figure 6:
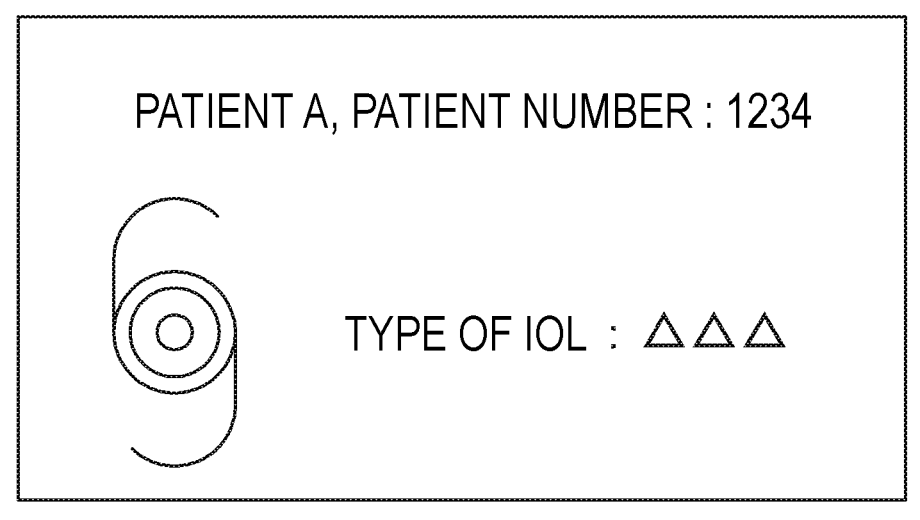

The management server 900 is connected to the ophthalmologic measurement apparatus 1 (refer to FIG. 1). The management server 900 may be a general computer or a tablet computer, or may be an ophthalmologic apparatus different from the ophthalmologic measurement apparatus 1. In addition, the management server 900 may be a part of a management system that manages patient information. For example, the management server 900 stores which IOL is inserted into any subject eye. For example, as illustrated in FIG. 6, the management server 900 stores a patient number (patient ID) registered for each patient and IOL information including a type of the IOL in a state where both are associated with each other. As the IOL information, the management server 900 may store power of the IOL or an orientation of the IOL (rotation angle around the optical axis of the IOL).

<Control Operation>

Figure 7:
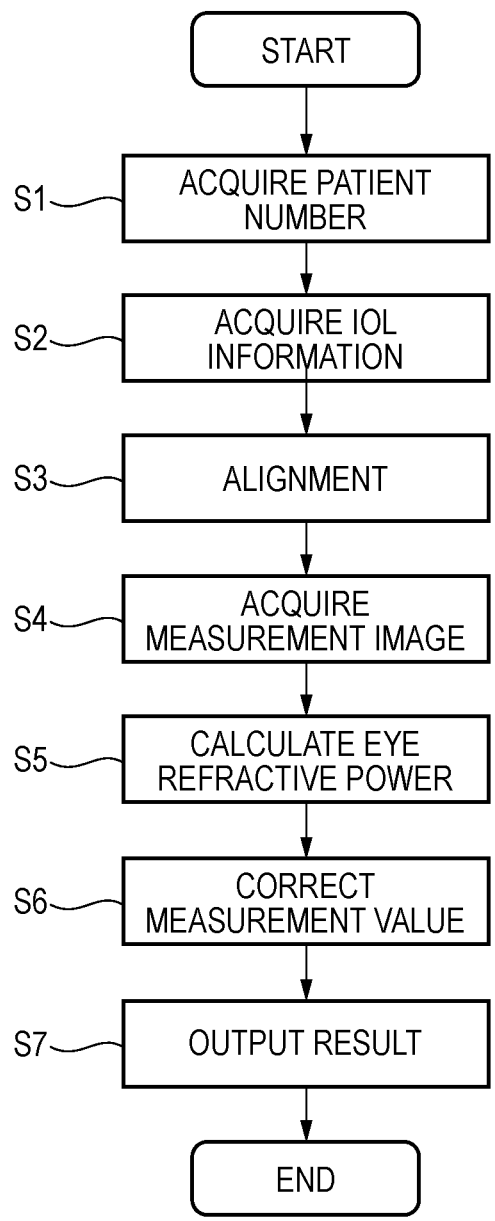
FIG. 7 is a flowchart illustrating a control operation.

Subsequently, a control operation of the ophthalmologic measurement apparatus 1 will be described with reference to FIG. 7. In the following description, a case of measuring the eye refractive power of the subject (patient) after the IOL is inserted by performing a cataract surgery will be described as an example.

(Step S1: Patient Number Acquisition)

First, an examiner operates the operation unit 76 to input a patient number of the patient who is the subject. The control unit 70 receives an operation input from the operation unit 76, and acquires the patient number of the patient. In this manner, the control unit 70 recognizes which patient's objective value is to be measured. The examiner may input the patient number by using a device such as a barcode reader.

(Step S2: IOL Information Acquisition)

When the control unit 70 acquires the patient number of the patient who is the subject, the control unit 70 acquires IOL information, based on the patient number. For example, the control unit 70 transmits the patient number to the management server 900, and requests for the IOL information. When the management server 900 receives the patient number from the control unit 70, the management server 900 reads the IOL information associated with the patient number, and transmits the IOL information to the control unit 70. In this manner, the control unit 70 acquires information such as a type of the IOL inserted into the subject eye.

(Step S3: Alignment)

Next, the control unit 70 turns on the point light source included in the index projection optical system 400. In this manner, an alignment index image is projected onto the cornea of the subject eye E. The examiner instructs the subject to fix his or her face to the face support unit 3 and to observe the fixation target formed in the fixation target plate 302. Infinitely and finitely distant alignment index images are projected onto the anterior segment of the subject eye E. The anterior segment of the subject eye E is detected by the image sensor 502 included in the observation optical system 500, and an anterior segment image is displayed on the display unit 75. The control unit 70 detects a deviation amount in alignment of the measurement unit 100 with respect to the subject eye E, based on a positional relationship of an alignment index detected from the anterior segment image. The control unit 70 controls the drive unit 4, based on the detected deviation amount, and three-dimensionally drives the measurement unit 100 to perform the alignment with respect to the subject eye E. As a matter of course, the examiner may manually perform the alignment by operating the operation unit 76.

(Step S4: Measurement Image Acquisition)

Next, the control unit 70 acquires a measurement image for measuring the eye refractive power of the subject eye E. For example, the control unit 70 causes the light source 211 to irradiate the subject eye E with the measurement light. The measurement light reaches the fundus Ef, and reaches the image sensor 226 via the ring lens 225 after being reflected by the fundus Ef. In this manner, the image sensor 226 acquires a pattern image (for example, a ring image) as the measurement image. The acquired ring image is stored in the memory 74. A size or a shape of the ring image varies in accordance with the eye refractive power of the subject eye E. For example, when the subject eye E is the hyperopia, the ring image enlarged in accordance with the spherical power is acquired. When the subject eye E is the myopia, the ring image downsized in accordance with the spherical power is acquired. In addition, when the subject eye E has astigmatism, the ring image has an elliptical shape in accordance with the cylindrical power, and the ring image tilted in accordance with the astigmatic axis angle is acquired.

(Step S5: Eye Refractive Power Calculation)

The control unit 70 calculates the eye refractive power, based on the acquired measurement image. For example, the control unit 70 specifies a position of the ring image in each meridian direction by thinning lines. For example, the position of the ring image may be specified by obtaining a peak value of a luminance signal or a position of the center of gravity. The control unit 70 performs ellipse fitting by using a least squares method, based on the position of the specified ring image, and obtains the eye refractive power in each meridian direction from an approximated elliptical shape. When the control unit 70 obtains the eye refractive power, the control unit 70 stores the eye refractive power in the memory 74.

(Step S6: Measurement Value Correction)

The control unit 70 corrects the measurement value of the calculated eye refractive power. For example, the control unit 70 reads a correction amount according to the type of the IOL which is acquired in Step S2 from a correction table stored in the memory 74, and corrects the eye refractive power calculated in Step S5. For example, when the measurement value is −0.75 D and the correction amount is −0.5 D, the correction amount is subtracted from (or added to) the measurement value, and the corrected measurement value becomes −0.25 D. The control unit 70 stores the corrected measurement value in the memory 74.

(Step S7: Result Output)

Figure 8:
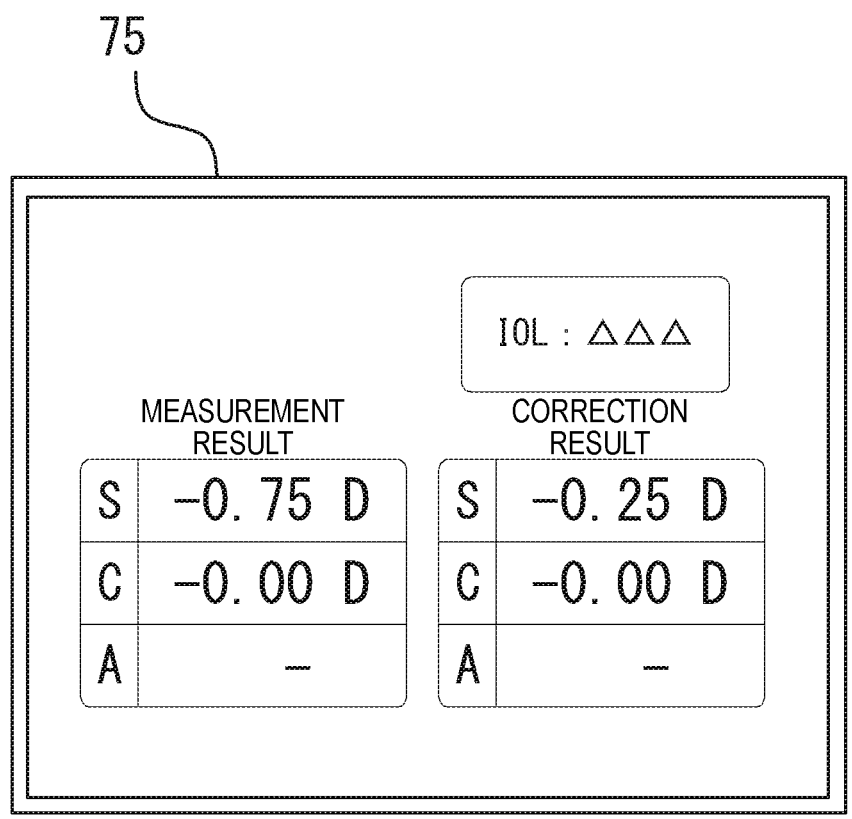
FIG. 8 is an example of a display screen of a measurement result.

The control unit 70 calls the corrected measurement value from the memory 74, and outputs the corrected measurement value as a correction result. For example, the control unit 70 causes the display unit 75 to display the correction result. As illustrated in FIG. 8, the control unit 70 may display both the measurement value before correction and the measurement value after correction. For example, the control unit 70 may cause a display screen to simultaneously display the spherical power (SPH), the cylindrical power (CYL), and the astigmatic axis angle (AXIS) before the correction together with the SPH, the CYL, and the AXIS after the correction. In addition, the control unit 70 may display the IOL information (for example, a type) inserted into the subject eye on the screen. As a matter of course, when the IOL does not require the correction, the correction result may not be displayed.

As described above, according to the ophthalmologic measurement apparatus 1 of the present example, the objective refractive power can be corrected for each lens-inserted eye that is the subject eye into which the IOL is inserted, in accordance with the type of IOL. Therefore, the more accurate measurement result can be acquired than that in the related art.

Figure 9:
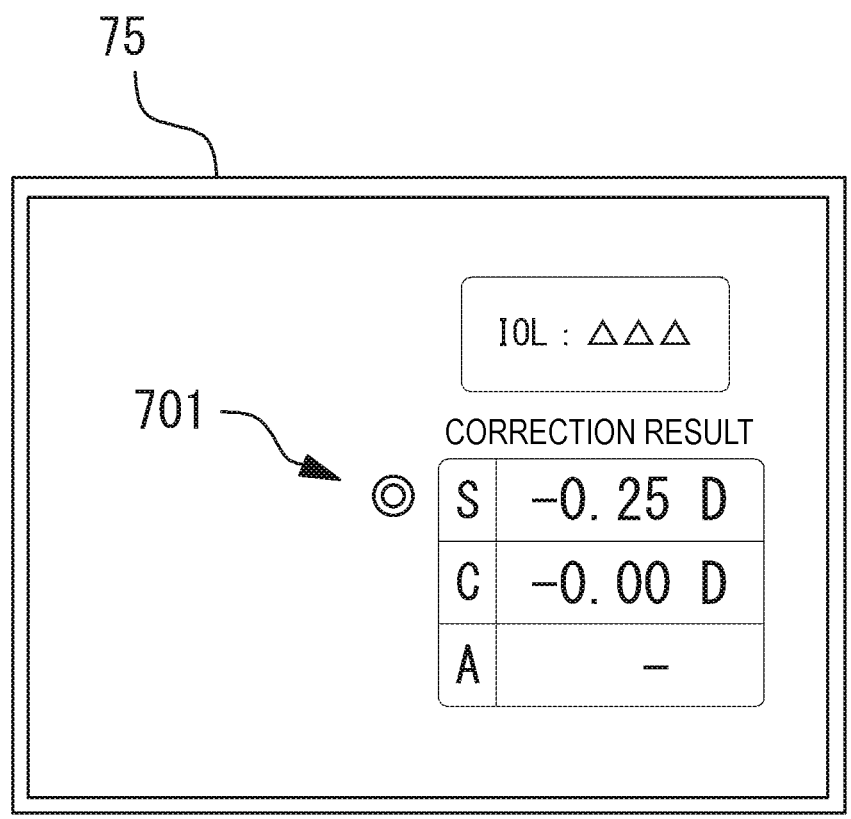
FIG. 9 is an example of a display screen of a measurement result.

As described above, when both the measurement values before and after the correction are not displayed, the control unit 70 may notify a user of whether or not the displayed measurement values has been corrected. For example, as illustrated in FIG. 9, the control unit 70 may indicate whether or not the measurement values has been corrected by displaying a correction mark 701 in the vicinity of the measurement value when the measurement value has been corrected, and by not displaying the correction mark 701 when the measurement value is not corrected. As a matter of course, the control unit 70 may not display the correction mark 701 when the measurement value has been corrected, and may display the correction mark 701 when the measurement value is not corrected, this manner, the control unit 70 may indicate whether or not the measurement value has been corrected. In this manner, it is possible to easily recognize whether or not the displayed measurement value has been corrected. A method of notifying the examiner is not limited to the display on the display unit 75, and the examiner may be notified by using a speaker, a lamp, or a printer.

The deviation amount of the diffractive IOL is changed depending on a pupil diameter of the subject. For example, when the pupil diameter of the subject eye is large, the deviation amount is likely to be affected by spherical aberration. When the pupil diameter is small and the measurement is performed with a paraxial ray (ray passing near the optical axis and forming a small angle with the optical axis), the deviation amount is less likely to be affected by the spherical aberration. Accordingly, the measurement value may deviate. Therefore, for example, the control unit 70 may acquire the pupil diameter of the subject eye by analyzing the anterior segment image at the time of the measurement, and may adjust the correction amount of the measurement value, based on a size of the pupil diameter.

The measurement value may deviate even when an incident angle of the ray into the IOL is changed by a radius of curvature of the cornea. Accordingly, the control unit 70 may adjust the correction amount of the measurement value in accordance with the radius of curvature of the cornea of the subject eye.

Figure 10:
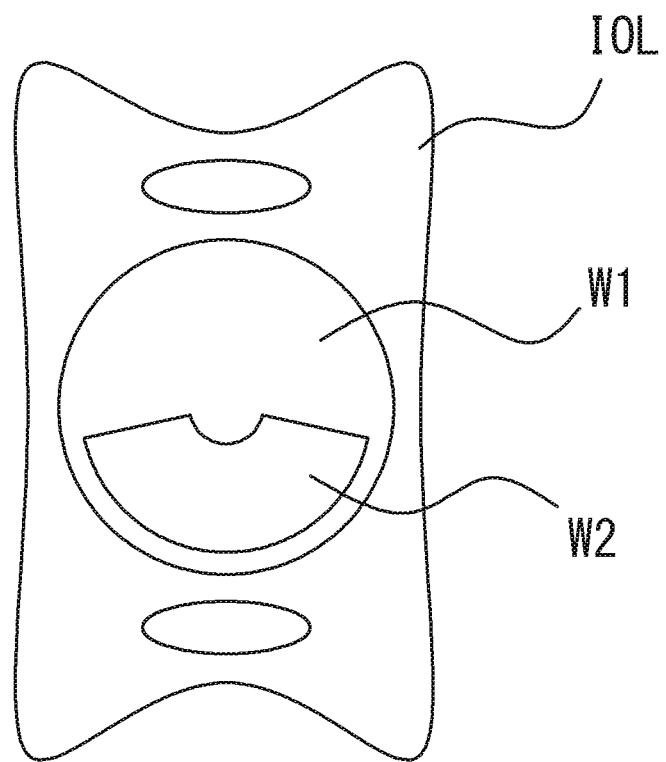
FIG. 10 is an example of a segmental IOL.

In the above-described example, the lens-inserted eye that is the subject eye when the diffractive multifocal IOL is inserted has been mainly described. However, even when another IOL is inserted, the correction data is stored in the memory 74 in advance. In this manner, the measured objective value can be easily corrected. For example, as illustrated in FIG. 10, when a segmental IOL having a different refractive power for each region (for example, a long-sight portion W1 and a short-sight portion W2) is inserted, the refractive power is divided into the long-sight power and the short-sight power to calculate an average of the measurement values. Accordingly, the SPH is small as the long-sight power, and the measurement value is calculated as the power in which the CYL occurs. Therefore, the control unit 70 may correct the long-sight power (SPH, CYL, and AXIS), based on the correction amount stored in the memory 74 in advance in accordance with the deviation amount of the refractive power. As a matter of course, the control unit 70 may calculate not only the long-sight power but also the short-sight power (refractive power for short-sight). In this case, the memory 74 may store each of the correction amount for calculating the long-sight power and the correction amount for calculating the short-sight power. In a case of the segmental IOL, a direction of astigmatism is changed depending on an orientation of the IOL inserted into the subject eye (rotation angle around the optical axis of the IOL). Therefore, the control unit 70 may correct the CYL and the AXIS, based on the correction amount set in accordance with the orientation of the IOL.

In the above description, the control unit 70 causes the display unit 75 to output the measurement value. However, the present disclosure is not limited thereto. For example, the control unit 70 may output the measurement value by storing in an external memory (for example, a USB memory), transmittance to other devices, or printing using a printer.

In the above-described example, the control unit 70 automatically acquires the IOL information from the management server 900, based on the patient number. However, the examiner may manually input the IOL information. For example, the control unit 70 may cause the display unit 75 to display the IOL selection screen. The IOL selection screen is a screen for selecting a type of the IOL inserted into the subject. For example, various types of the IOL are displayed on the IOL selection screen, and the examiner selects the IOL inserted into the subject eye E. In this manner, even when the IOL is not connected to the management server 900, the information of the IOL inserted into the subject eye can be acquired, and the measurement value of the eye refractive power can be properly corrected, based on the information.

A configuration may be adopted so that the IOL information (type of the IOL) stored in the memory 74 and the correction amount corresponding thereto can be added later. For example, a configuration may be adopted so that the examiner may newly register the IOL information and the correction amount by operating the operation unit 76. In this case, the control unit 70 causes the memory 74 to store the IOL information and the correction amount which are input by the examiner. As a matter of course, the control unit 70 may acquire the IOL information and updated information of the correction amount from an external storage device such as the management server 900, and may automatically update the information of the memory 74.

In the above example, the correction amount is stored in the memory 74 of the ophthalmologic measurement apparatus 1. However, the present disclosure is not limited thereto. For example, the control unit 70 may acquire the correction amount corresponding to the IOL of the subject from the external storage device such as the management server 900 when the measurement value is corrected.

The anterior segment image captured by the observation optical system 500 may be the transillumination image. For example, the transillumination image is an intra-pupil image captured by illuminating an inner portion of the pupil with fundus reflected light. In this case, the control unit 70 may determine the type of IOL, based on the transillumination image. For example, the control unit 70 may determine the type of IOL by analyzing a luminance distribution of the transillumination image and detecting a structure of the IOL, based on a position where luminance is changed. For example, the control unit 70 may automatically acquire the correction amount corresponding to the type of IOL which is determined based on the transillumination image.

The present disclosure is not limited to the above-described example, and various modifications can be made. For example, a configuration may be adopted so that software (program) for realizing functions of the above-described example is supplied to a system or a device via a network or various storage media, and a computer (or a CPU or an MPU or the like) of the system or the device reads and executes the program.

What is claimed is:

1. An ophthalmologic measurement apparatus for measuring a subject eye in which an intraocular lens is inserted, comprising:
    an optical system that objectively measures eye refractive power of the subject eye; and
    a controller comprising a processor and memory, wherein the controller is configured to:
        determine intraocular lens information relating to the intraocular lens inserted into the subject eye based on a transillumination image of the subject eye, wherein the transillumination image is an intra-pupil image captured by illuminating an inner portion of the pupil with fundus reflected light,
        acquire a deviation amount between visible light and infrared light for the intraocular lens inserted into the subject eye, and
        correct a measurement result of the eye refractive power based on the deviation amount.

2. The ophthalmologic measurement apparatus according to claim 1,
    wherein the intraocular lens information includes a type of the intraocular lens, and
    wherein the controller is configured to correct the measurement result, based on a correction amount set in accordance with the type.

3. The ophthalmologic measurement apparatus according to claim 1,
    wherein the intraocular lens information includes a rotation angle around an optical axis of the intraocular lens in an intraocular part of the subject eye, and
    wherein the controller is configured to correct the measurement result, based on a correction amount set in accordance with the rotation angle.

4. The ophthalmologic measurement apparatus according to claim 1,
    wherein the controller is configured to acquire the intraocular lens information from a management server in which the intraocular lens information is stored.

5. The ophthalmologic measurement apparatus according to claim 1,
    wherein the controller is configured to acquire identification information for identifying a subject to acquire the intraocular lens information associated with the subject by the identification information.

6. The ophthalmologic measurement apparatus according to claim 1, further comprising:
    the controller is configured to receive an operation input from an examiner, and
    wherein the controller is configured to acquire the intraocular lens information, based on the operation input.

7. The ophthalmologic measurement apparatus according to claim 6, further comprising:
    that the controller is configured to cause a display to display an IOL selection screen for selecting a type of the intraocular lens inserted into the subject eye.

8. The ophthalmologic measurement apparatus according to claim 1, further comprising:
    an output unit that outputs both the measurement result obtained before correction and a correction result obtained after correcting the measurement result.

9. The ophthalmologic measurement apparatus according to claim 1, further comprising:
    a notification unit that notifies a user of whether or not the measurement result has been corrected.

10. An ophthalmologic measurement system comprising:
    an ophthalmologic measurement apparatus that measures a subject eye in which an intraocular lens is inserted; and
    a management server that stores intraocular lens information relating to the intraocular lens inserted into the subject eye,
    wherein the management server includes storage that stores the intraocular lens information in a state where the intraocular lens information is associated with identification information for identifying a subject, and
    wherein the ophthalmologic measurement apparatus includes:
        an optical system that measures eye refractive power of the subject eye; and
        a controller comprising a processor and memory and configured to:
            acquire the identification information,
            determine the intraocular lens type based on a transillumination image of the subject eye, wherein the transillumination image is an intra-pupil image captured by illuminating an inner portion of the pupil with fundus reflected light,
            acquire a deviation amount between visible light and infrared light for the intraocular lens inserted into the subject eye; and
            correct a measurement result of the eye refractive power, based on the deviation.

11. A non-transitory computer-readable medium storing an ophthalmologic measurement program, the ophthalmologic measurement program being executed by a processor in an ophthalmologic measurement apparatus for measuring a subject eye in which an intraocular lens is inserted to cause the ophthalmologic measurement apparatus to execute a process comprising:
    a measurement step of measuring eye refractive power of the subject eye;
    a determination step for determining intraocular lens information relating to an intraocular lens inserted into the subject eye based on a transillumination image of the subject eye, wherein the transillumination image is an intra-pupil image captured by illuminating an inner portion of the pupil with fundus reflected light,
    an acquisition step for acquiring a deviation amount between visible light and infrared light for the intraocular lens inserted into the subject eye; and
    a correction step of correcting a measurement result of the eye refractive power, based on the deviation amount.

12. The ophthalmologic measurement apparatus according to claim 1, wherein the controller is configured to correct the measurement result of the eye refractive power by subtracting or adding, from the measurement result of the eye refractive power, a correction amount according to a type of intraocular lens.

13. The ophthalmologic measurement apparatus according to claim 1, wherein the optical system that objectively measures eye refractive power of the subject eye comprises a light projecting optical system and a light receiving optical system, wherein the light projecting optical system is configured to project a measurement light flux onto a fundus of the subject's eye and the light receiving optical system is configured to extract a reflected light flux of the measurement light flux reflected by the fundus.

14. The ophthalmologic measurement apparatus according to claim 1, wherein the controller is configured to determine the intraocular lens information by analyzing a luminance distribution of the transillumination image and detecting a structure of the IOL based on a position where luminance is changed.

15. The ophthalmologic measurement system according to claim 10, wherein the controller is configured to determine the intraocular lens type by analyzing a luminance distribution of the transillumination image and detecting a structure of the IOL based on a position where luminance is changed.

16. The non-transitory computer-readable medium according to claim 11, wherein the a determination step determines the intraocular lens information by analyzing a luminance distribution of the transillumination image and detecting a structure of the IOL based on a position where luminance is changed.

17. The ophthalmologic measurement system according to claim 10, wherein the ophthalmologic measurement apparatus further comprises an output unit that outputs the measurement result obtained before correction and a correction result obtained after correcting the measurement result.

18. The non-transitory computer-readable medium according to claim 11, where the process further comprises outputting the measurement result obtained before correction and a correction result obtained after correcting the measurement result.

* * * * *